(12) United States Patent
Fredenberg

(10) Patent No.: US 6,886,407 B1
(45) Date of Patent: May 3, 2005

(54) NONDESTRUCTIVE EXAMINATION OF HIGH PRESSURE TURBINE CYLINDERS

(75) Inventor: Richard Wayne Fredenberg, Harrison City, PA (US)

(73) Assignee: Westinghouse Electric Company LLC, Pittsburgh, PA (US)

(*) Notice: Subject to any disclaimer, the term of this patent is extended or adjusted under 35 U.S.C. 154(b) by 59 days.

(21) Appl. No.: 10/646,136

(22) Filed: Aug. 22, 2003

(51) Int. Cl.$^7$ .............................................. G01N 29/10
(52) U.S. Cl. ..................................... 73/622; 73/865.8
(58) Field of Search ........................ 73/579, 583, 587, 73/593, 601, 622–623, 627–629, 633–634, 589, 660, 865.8

(56) References Cited

U.S. PATENT DOCUMENTS

| | | | | |
|---|---|---|---|---|
| 4,597,294 A | * | 7/1986 | Brill et al. ...................... | 73/623 |
| 4,598,580 A | | 7/1986 | Alkire et al. | |
| 4,663,727 A | * | 5/1987 | Saporito et al. .............. | 702/39 |
| 4,955,235 A | * | 9/1990 | Metala et al. .................. | 73/601 |
| 5,408,883 A | * | 4/1995 | Clark et al. .................... | 73/601 |
| 5,445,027 A | * | 8/1995 | Zorner .......................... | 73/593 |
| 6,487,922 B1 | | 12/2002 | Bauer et al. | |

OTHER PUBLICATIONS

Lareau et al., Phased Array Imaging First Use Quantification Effort: BWR Feedwater Nozzle Inner Radius Inspection from Vessel OD for a US Nuclear Power Plant, NDT.net—May 2002, vol. 7 No. 5. found at www.ndt.net/article/v07n05/olis/olis.htm.

Poguet et al., Phased Array Technology: Concepts, Probes and Applications, ndt.net—May 2002, vol. 7 No. 5, found at www.ndt.net/article/article/v07n05/poguet.htm.

Francois, Ultrasound Phased Array, NDT.net—May 2002, vol. 7 No. 5, R/D Tech's Technology Information, found at www.ndt.net/article/v07n05/rdtech/rtech.htm.

Wustenberg et al., Scanning Modes at the Application of Ultrasonic Phased Array Inspection Systems, found at www.ndt.net/article/wcndt00/papers/idn193/idn193.htm.

EPRI News Release, Phased Array Ultrasonic Technique from EPRI Improves Turbine Disk Inspection, found at www.epri.com/corporate/discover epri/news/releases/991216 phased.htm.

Kawanami et al., Development of Phased–Array Ultrasonic Testing Probe, Mitsubishi Heavy Industries, Ltd., Technical Review vol. 38 No. 3, pp. 121–125 (Oct. 2001).

NDT Resource Center, Inspection Using Magnetic Rubber, found at www.ndt–ed.org/EducationResources/Community College/MagParticle/Testing Practi . . . .

E1444–01 Standard Practice for Magnetic Particles Examination, Copyright 2003 ASTM International, Book of Standard Volumes 3.03, found at www.astm.org/ cgi–bin/Soft-Cart.exe/DATABASE.CART/REDLINE Pages/E1444.

Magnetic Particle Inspection. AC 43–13–1B, found at www1.faa.gov/avt/afs/300/pdf/2a–ch5.pdf, pp. 5–19 to 5–30.

\* cited by examiner

*Primary Examiner*—Helen Kwok

(57) ABSTRACT

A method of inspecting the steam inlet sleeves on high pressure outer cylinders and the nozzle chamber to cylinder welds on the high pressure steam turbines using linear phased array ultrasonic transducers. The transducers are supported on the surface of the component to be monitored. The transducers are then move axially while monitoring the transducer's output to identify the location to be monitored. The axial extent of the transducers are then fixed and the transducers are moved circumferentially around the surface of the component at least 360° while noting outputs of the transducers indicative of fatigue-induced flaws. The transducers are then routed to the location on the wall of the component where the most significant flaw was noted. Then the transducers are successively focused at different depths in the wall where the most significant flaw was identified to further characterize the depth and size of the flaw.

14 Claims, 7 Drawing Sheets

NONDESTRUCTIVE EXAMINATION OF HIGH PRESSURE TURBINE CYLINDERS

BACKGROUND OF THE INVENTION

1. Field of the Invention

This invention pertains in general to the nondestructive examination of high pressure turbine outer cylinders and more particularly to the nondestructive examination of the main steam inlet sleeves on Westinghouse high pressure outer cylinders and nozzle chamber to cylinder welds on the high pressure inner cylinders, employing linear phased ultrasonic transducer arrays.

2. Related Art

Westinghouse and its subsidiaries have been inspecting the steam inlet components of Westinghouse turbine high pressure cylinders since the 1970s employing as its primary means of inspection of the trepan region of the main steam inlet nozzle a magnetic rubber inspection process. The main areas of concern are the trepan region of the main steam inlet sleeves on the high pressure outer cylinder and the nozzle chamber to cylinder welds on the high pressure inner cylinder. These regions are the areas of maximum stress build-up. The nozzle to inner cylinder welds are inspected using flexible fiber optics, ultrasonic transducers and a radiological examination process.

The magnetic rubber inspection process requires two days of examinations plus a day for dust blasting. The process also requires two 440 volt set-ups for the magnetizing equipment employed to induce a magnetic field on the area to be inspected. The magnetic rubber inspection process provides a good surface examination but the sensitivity is dependent on the adequacy of the magnetic field that is induced that cannot be accurately verified.

The magnetic rubber inspection technique uses a liquid (uncured) rubber containing suspended magnetic particles. The rubber compound is applied to the area to be inspected on a magnetized component. Inspections can be performed using either an applied magnetic field, which is maintained while the rubber sets, or a residual field from magnetization of the component prior to or shortly after pouring the compound. This latter technique is employed in inspecting the Westinghouse turbines. A dam of modeling clay, or an inflatable dam such as that described in U.S. Pat. No. 4,598,580, is often used to contain the compound in the region of interest. The rubber is allowed to set, which takes approximately two hours, and then the rubber cast is removed from the part. The rubber conforms to the surface contours and provides a reverse replica of the surface. The rubber cast is examined for evidence of discontinuities, which appear as lines on the surface of the molding. The molding can be retained as a permanent record of the inspection.

Magnetic particle inspection uses the tendency of magnetic lines of force, or flux, of an applied field to pass through the metal rather than through the air. A defect at or near the metal surface distorts the distribution of the magnetic flux and some of the flux is forced to pass out through the surface. The field strength is increased in the area of the defect and opposite magnetic poles form on either side of the defect. Fine magnetic particles within the uncured rubber solution applied to the part are attracted to these regions and form a pattern around the defect. The pattern of particles is maintained by the induced magnetic field until the rubber cures and permanently captures the pattern as a visual indication of a defect. Operators employing magnetic particle inspection have to recognize nonrelevant error indications during examination. Proper analysis of indications in these regions will require considerable skill and experience and supplemental examination methods are required before a final evaluation can be made. The technique cannot be used to determine flaw depth which further complicates interpretation of the indications.

A visual inspection of the nozzle chamber to inner cylinder welds is made using flexible fiber optics to examine the root of the welds for service induced cracks; ultrasonic transducers are used to further verify cracks on the sheer plane emanating from the weld fillet radius of the trepan; and a radiological examination is performed to identify cracks running radially into the weld or adjacent areas.

The time to perform these inspections typically takes two to three days and can fall within the critical path of an outage. The radiological portion of the examination requires that the cylinder has to be isolated from all other work being performed and thus can delay work being performed in parallel. The work can be further held up if the equipment to perform the radiological exam or to magnetize the part is not timely available. Furthermore, these examinations do not provide crack depth information which complicates the characterizations of aberrations on the surface that might be noted, as flaws induced by fatigue.

Any fatigue-induced crack formed in either the trepan region of the sleeves or the nozzle chamber to cylinder welds necessitates replacement of the main steam inlet nozzle which can cost in the order of magnitude of $250,000 and significantly extend an outage. Therefore, it is important that aberrations detected during the nondestructive examination be properly characterized.

Accordingly, it is an object of this invention to provide an improved nondestructive examination process for identifying cracks in the main steam inlet nozzle sleeves and nozzle chamber to cylinder welds of high pressure turbines that does not require surface preparation such as the dust blasting step required for the magnetic rubber inspection process.

It is a further object of this invention to provide an improved inspection technique that significantly reduces the time to inspect the main steam inlet nozzle sleeves and nozzle chamber to cylinder welds of high pressure turbines.

It is a further object of this invention to provide such an improved nondestructive examination procedure that will identify the depth of any anomaly noted in the main steam inlet nozzle sleeves and the nozzle chamber to cylinder welds of high pressure turbines that will permit more accurate characterization of the anomalies as fatigue-induced flaws.

SUMMARY OF THE INVENTION

The foregoing objects can be achieved by the method of this invention for inspecting a cylinder component of high pressure cylinders of steam turbines and more particularly, the main steam inlet nozzle sleeves on high pressure outer cylinders and the nozzle chamber to cylinder welds on the high pressure inner cylinders, using linear phased array ultrasonics. The method comprises the steps of supporting a linear phased array of ultrasonic transducers at a first axial location on the surface of the cylinder component and moving the linear phased array of ultrasonic transducers axially while monitoring the linear phased array of ultrasonic transducers' outputs to identify from the outputs the axial location to be monitored. The linear phased array of ultrasonic transducers are then fixed at the axial location to be monitored and are rotated circumferentially around the surface of the cylinder component at least 360° while the outputs of the linear phased array of ultrasonic transducers are monitored to note indications indicative of fatigue-induced flaws in the wall of the cylinder component. The linear phased array of ultrasonic transducers is then routed circumferentially around the fixed axial location to the location on the surface of the cylinder component where the most significant flaw was noted during the previous step. At the location where the flaw was noted the linear phased array of ultrasonic transducers are successively focused at different depths in the wall to further characterize the depth and size of the flaw.

Preferably the linear phased array of ultrasonic transducers are supported on the inside surface of the cylinder component. However, where that is not possible, the linear phased array of ultrasonic transducers may be supported on the outside surface of the cylinder component. The phased array of ultrasonic transducers may be positioned and operated remotely especially where the geometry of the area to be inspected is not readily accessible. In the preferred embodiment the circumferential position of the phased array of linear transducers is encoded and recorded together with the data collected at the corresponding position on the surface of the cylinder components.

Where a significant indication of a potential flaw is detected a magnetic rubber nondestructive examination is conducted on the surface of the potential flaw. However, this additional step is only expected to be necessary in 10 percent of the cylinder components monitored. Thus, there is a substantial savings in inspection time achieved by the method of this invention along with improved confidence in the quality of the results.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
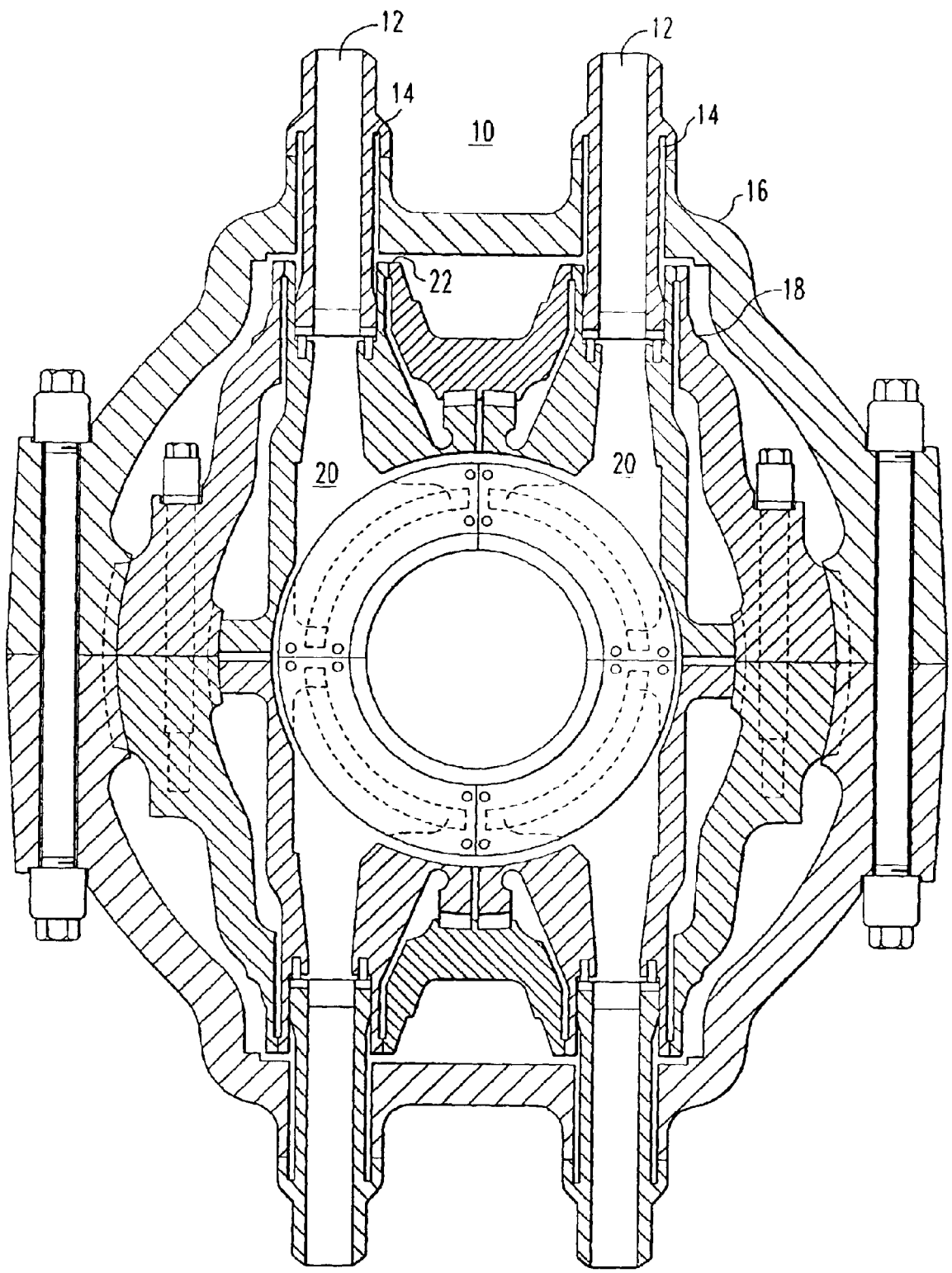
FIG. 1 is a cross-sectional view of a high pressure steam turbine taken through the main steam inlet nozzles.
Figure 2:
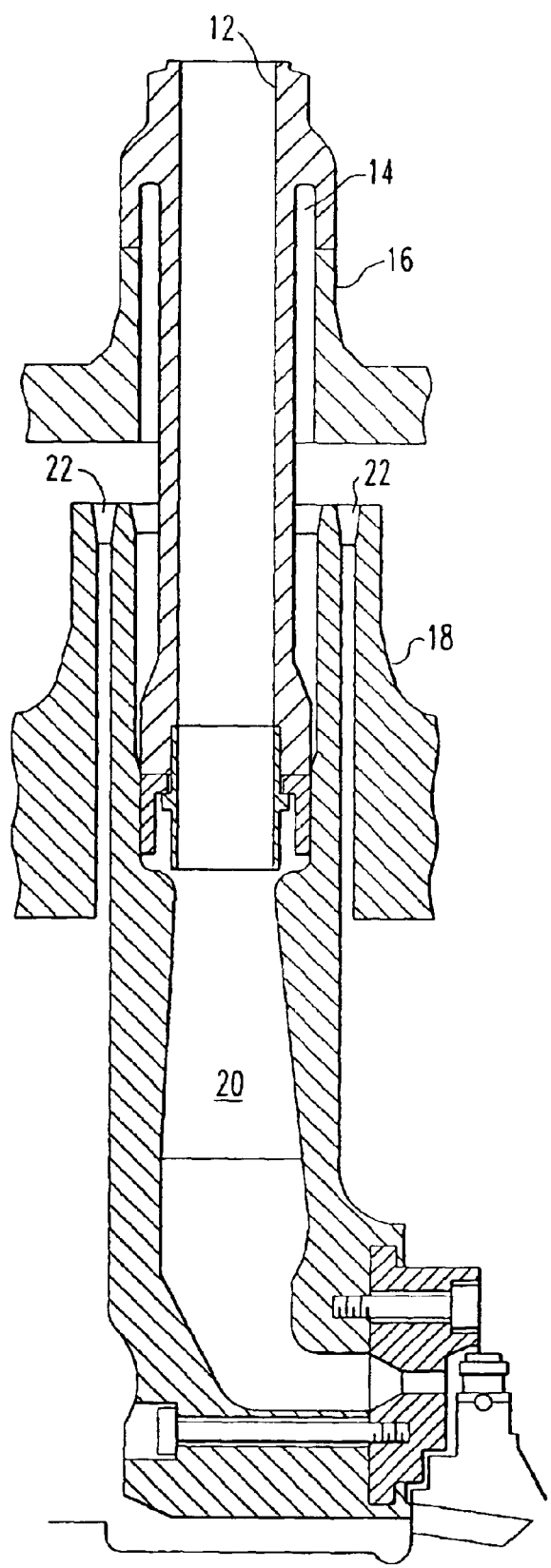
FIG. 2 is a schematic of a side view of the outer cylinder to main steam nozzle sleeve connection and of the nozzle chamber to inner cylinder connection shown in FIG. 1.

Experience has shown that high stresses develop in certain components of high pressure steam turbines that can cause metal fatigue resulting in cracks in the component walls. If unattended, these cracks can result in forced outages which are extremely expensive to the utilities that rely upon the steam turbines to drive generators to produce electricity. FIG. 1 shows a cross section of a high pressure steam turbine 10 having an outer cylinder 16 and an inner cylinder 18 and main steam inlet sleeves 12 which join the outer turbine at a trepan region 14. The main steam inlet sleeves 12 are connected to a nozzle chamber 20 which is coupled to an inner cylinder 18 by a fillet weld 22 which can be better observed in FIG. 2. FIG. 2 is a schematic illustration of the main steam inlet sleeve 12 and nozzle chamber 20 assembly shown coupled to the outer cylinder 16 at the trepan region 14 and to the inner cylinder 18 at the fillet weld 22. Experience has shown that the steam inlet sleeve 12 is susceptible to cracking in the trepan region 14 and that the fillet weld 22 is similarly susceptible to cracking. Off ine nondestructive examination of these regions during scheduled outages is recommended to avoid unscheduled shutdowns. Typical inspections in the past have taken between three and five days and has taken a somewhat subjective analysis to determine if fatigue cracks exists. No effective repair procedure exists. If a fatigue crack is noted the main steam inlet sleeve has to be replaced at a cost of approximately $250,000, which extends the outage to accommodate the repair. Therefore, it is extremely important to the utilities that the nondestructive examination of these areas be accurate and as objective as possible. To date, the nondestructive examination techniques that have been employed have disrupted work on the turbine that could otherwise be performed in parallel while the examination is in process. These techniques have not been able to identify the depth of flaws noted and thus make the characterization of a noted flaw as a fatigue crack extremely subjective.

Figure 3:
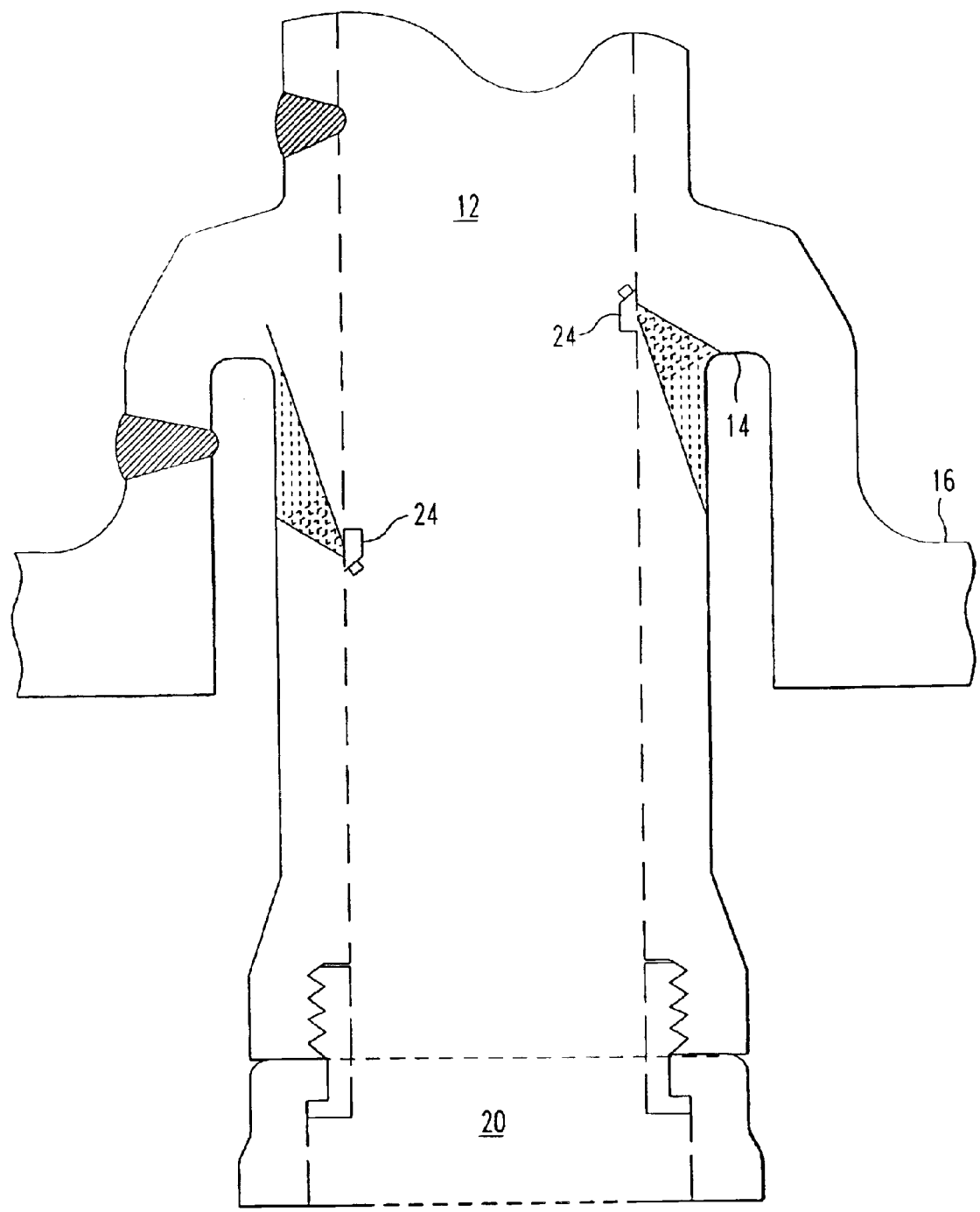
FIG. 3 is a schematic of a side view of a main steam nozzle trepan region being examined by two phased arrays of ultrasonic transducers positioned on the inside circumference of the nozzle sleeve surface axially aligned with the trepan region.

As shown in FIG. 3, this invention employs one or more linear phased arrays of ultrasonic transducers 24 on the inside circumference of the main steam inlet sleeves in the trepan region 14 to inspect the trepan area for cracks. The linear phased array of ultrasonic transducers is supported at an axial location on the surface of the main steam inlet sleeve and is moved axially with respect to the axis of the sleeve while its outputs are monitored to identify its proper positioning at the axial location to be monitored, in this case, the trepan region 14. Once the axial location is identified, the transducer's axial position is fixed and the linear phased array of ultrasonic transducers 24 is moved circumferentially around the surface of the sleeve 12 at least 360° while the outputs of the linear phased array of ultrasonic transducers indicative of a fatigue-induced flaw in the wall of the main steam inlet sleeve 12 is noted in a data collection system. The data is also viewed real time on a screen attached to the controller which is figuratively shown in FIG. 8A. If a fatigue-induced flaw is noted in the 360° circumferential scan the linear phased array of ultrasonic transducers 24 is routed circumferentially around the axial location along the inside surface of the main steam inlet sleeve 12 to the location where the most significant flaw was noted. The linear phased array of ultrasonic transducers is then successively focused at different depths in the wall where the most significant flaw was noted to further characterize the depth and size of the flaw. While two linear phased arrays of ultrasonic transducers are shown in FIG. 3, only one is necessary. Two are shown only to illustrate that the scan can be conducted at different angles.

Figure 4A:
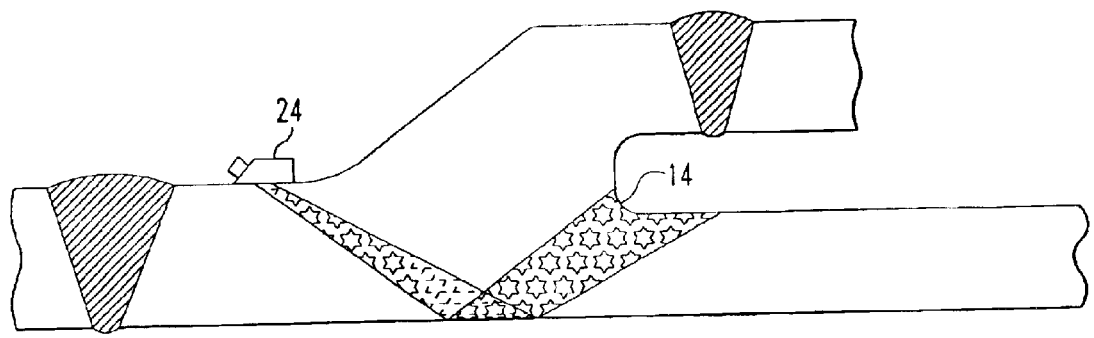
FIGS. 4A and 4B are schematic views of the trepan region of a steam inlet nozzle sleeve showing a phased array of ultrasonic transducers positioned on the outer circumferential surface of the sleeve at two different positions adjacent the trepan region.
Figure 4B:
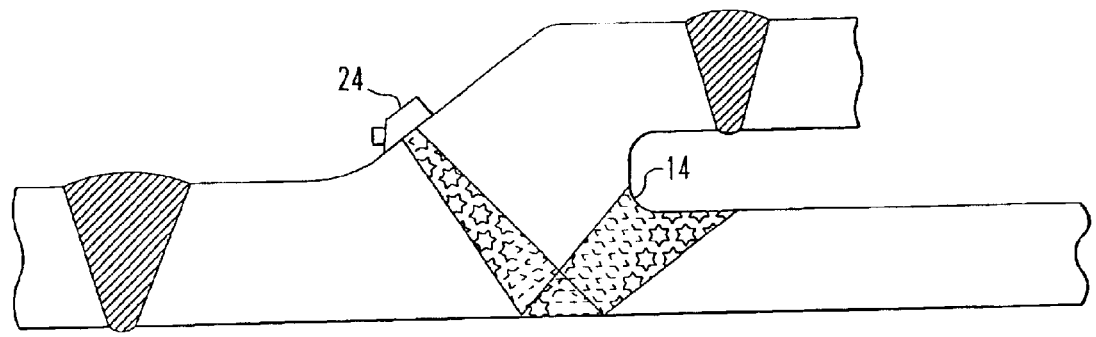

Some high pressure steam turbine designs without disassembly will permit access to the trepan region using the second leg of a refracted ultrasonic signal, that is transmitted from a focused linear array from the outside diameter surface of the main steam inlet pipe sleeve 12 as shown in FIG. 4. FIGS. 4A and 4B show two different angles of scan that can be employed for this purpose though it should be appreciated that the trepan region of the main steam inlet nozzle sleeve can be interrogated using a multitude of scan plans.

Figure 5:
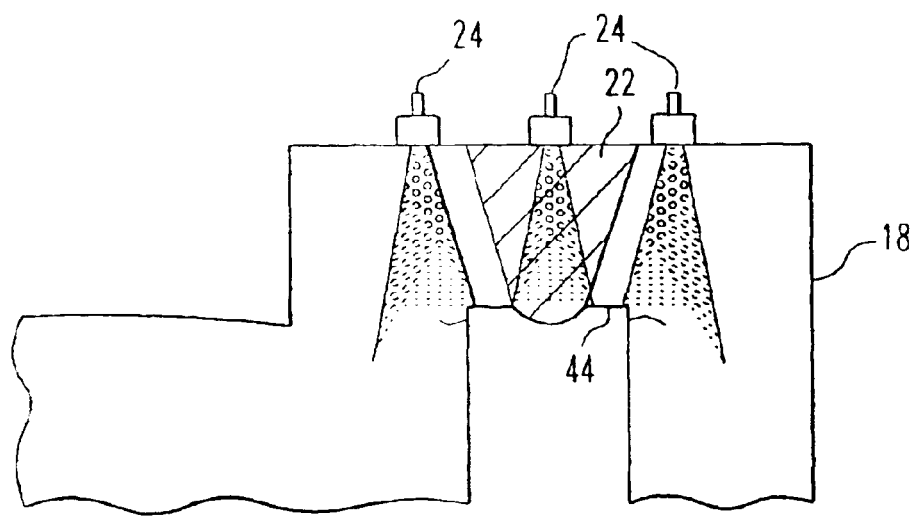
FIG. 5 is a schematic illustration of a nozzle chamber to cylinder weld being interrogated using focused longitudinal waves from several phased arrays of ultrasonic transducers.
Figure 6:
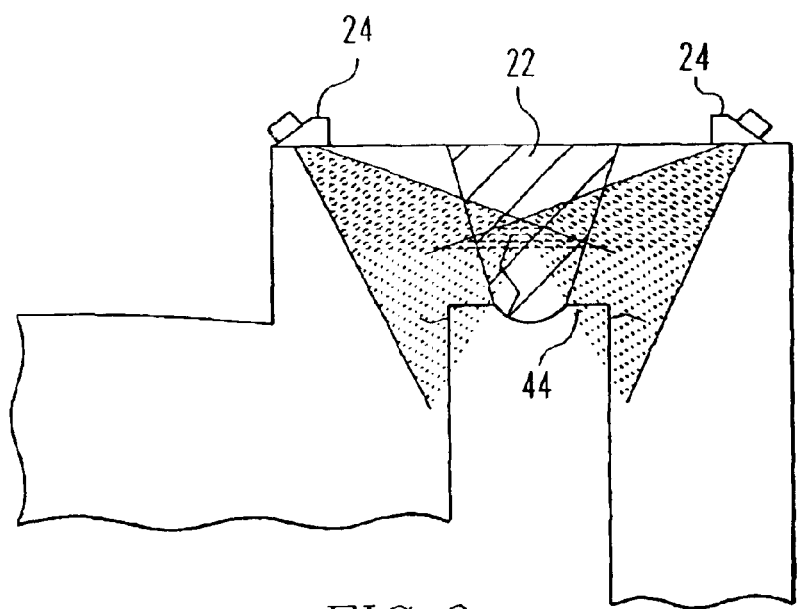
FIG. 6 is a schematic view of the nozzle chamber to cylinder weld illustrated in FIG. 5 with a pair of phased arrays of ultrasonic transducers shown focusing sheer waves across the weld.
Figure 7:
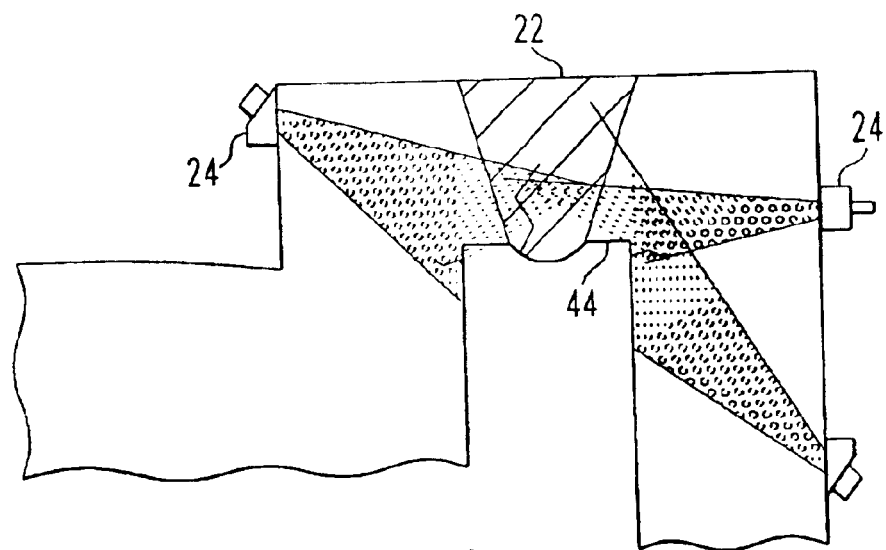
FIG. 7 is a schematic view of the chamber to cylinder weld illustrated in FIG. 5 being interrogated by two phased arrays of ultrasonic transducers employing sheer and/or longitudinal waves.

FIG. 5 illustrates one scan plan that can be employed for interrogating the trepan region 44 of the nozzle chamber to inner cylinder welds 22. Linear phased arrays 24 using focused longitudinal waves can be employed to inspect for cracks along the sheer plane as illustrated in FIG. 5. Three such arrays of transducers are shown to illustrate that the scans can be made at different radial positions around the exterior of the main steam inlet sleeve 12 over the trepan region 44 adjacent and over the nozzle chamber to inner cylinder welds 22. Similarly, sheer waves can be used across the top of the trepan region 44 as illustrated in FIG. 6. Additionally, sheer and/or longitudinal waves emanating from the inside diameter or outside diameter of the trepan region 44 can be employed for identifying cracks primarily on the radial plane as shown in FIG. 7. Remote visual equipment can be employed with this examination to confirm indications found using the linear phased array of ultrasonic transducers 24. The transducers preferably operate between 5 and 10 megahertz frequency and employ 32 transducer elements operating in a pitch/catch mode side-by-side design with a 16 element active aperture. A pulse/echo 32 element linear array may also be employed. Elements of this type can be purchase from Kraut Kramer Ultrasonic Systems, Agfa NDT Inc., Lewiston, Pa. and RD Tech, Idaho Falls, Id. Software for controlling the arrays and processing the outputs can be obtained from RD Tech.

Figure 8B:
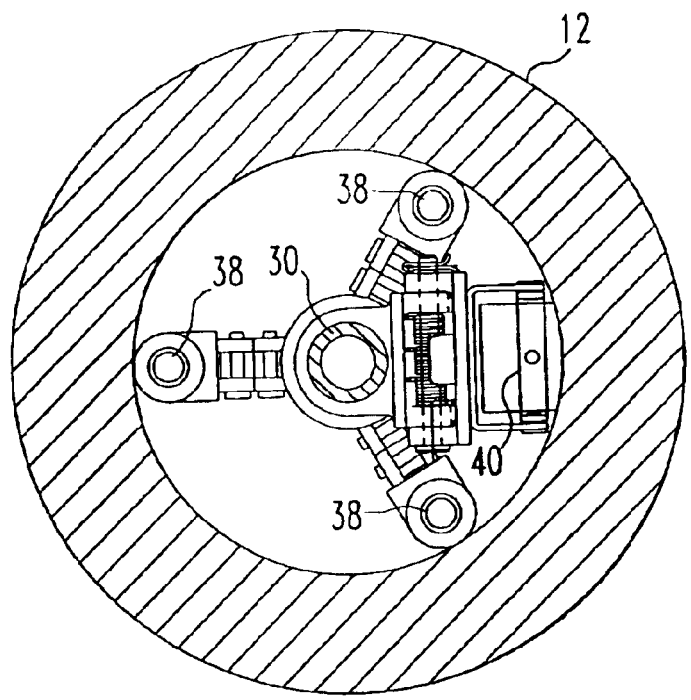
FIG. 8B is a cross sectional view of the nozzle bore scanner illustrated in FIG. 8A taken along the lines "A—A" thereof.
Figure 8A:
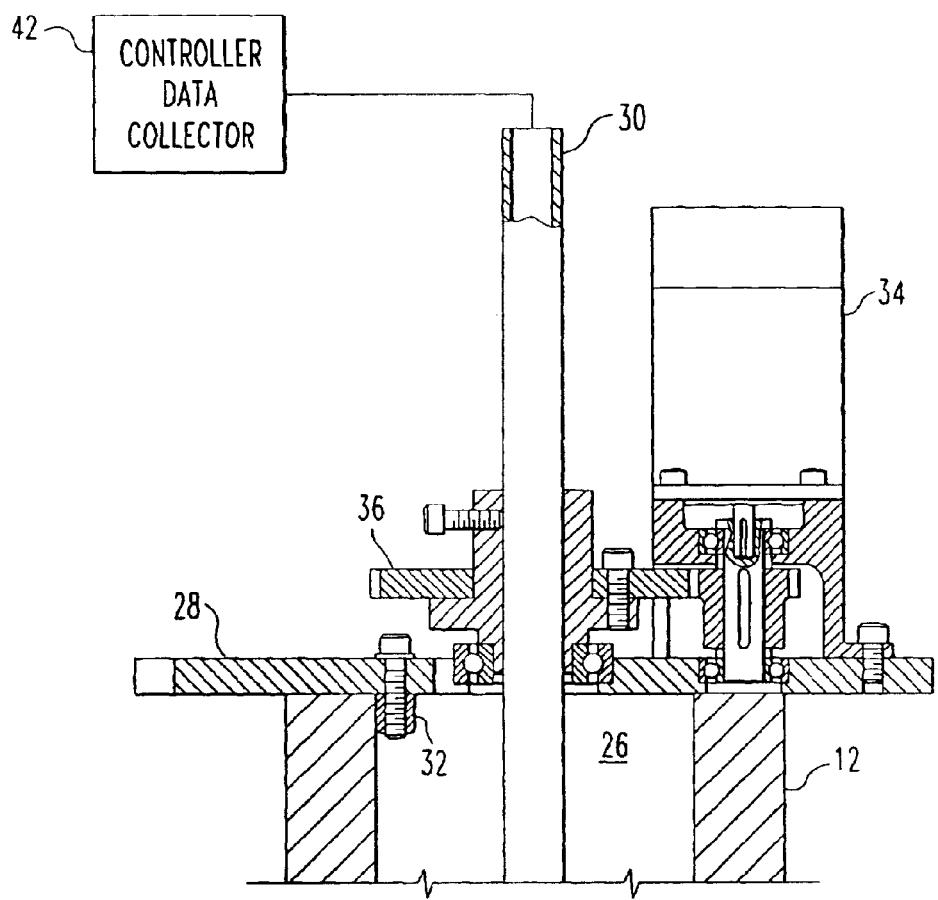
FIG. 8A is a schematic view of a nozzle bore scanner of this invention positioned within a main steam nozzle focusing a phased array of ultrasonic transducers on the trepan region.
Figure 8A:
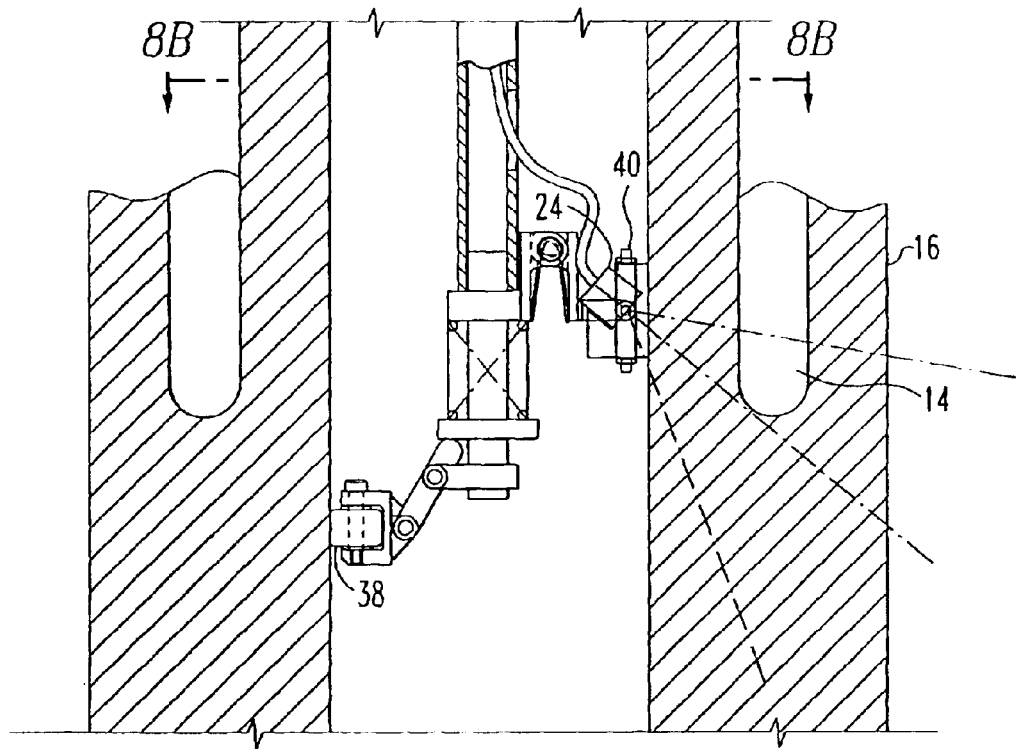

A nozzle bore scanner fixture 26 is illustrated in FIGS. 8A and 8B. The scanner fixture 26 axially locates the linear phased array of ultrasonic transducers 24 axially within the main steam inlet sleeve 12 until the linear phased array of ultrasonic transducers 24 is focused on the trepan region 14 of the main steam inlet nozzle sleeve 12. The linear phased array of ultrasonic transducers 24 is supported from a central tool post 30 which is suspended from a mounting plate 28 that interfaces with the face of the main steam inlet nozzle. An adjustable mounting lug 32 in the mounting plate 28 centers the tool post 30. The tool post 30 is moved axially as well as rotated to circumferentially position the ultrasonic probe 24 through a gear drive 36 and drive motor 34 which are secured to the mounting plate 28. Three spring-loaded centering guide rollers 38 are circumferentially positioned around the inner circumference of the main steam nozzle sleeve 12 to center the tool post 30. The centering of the tool post 30 by the spring-loaded centering guide rollers 38 can better be appreciated from the cross sectional view shown in FIG. 8B. A wedge 40 extending from the ultrasonic transducer probe bracket rides on the inner surface of the main steam inlet sleeve and dispenses a wetting solution that promotes coupling of the ultrasonic signal between the ultrasonic transducer probe 24 and the surface of the main steam inlet sleeve 12. Preferably, the wedge has the same contour as the inner surface of the main steam inlet sleeve 12, and promotes the coupling of the ultrasonic signal. The outputs from the ultrasonic transducer probe 24 are routed through the tool post 30 to a controller and data collector 42 that both collects and stores the data and controls the motor 34 to properly position the probe 24 in accordance with the steps of this invention. An encoder on the motor or one positioned on the guide rollers 38 can be used to accurately show the position of the linear phased array of ultrasonic transducers. Alternately, the motor 34 can be replaced with a hand wheel for manual operation.

While a specific embodiment of the invention has been described in detail, it will be appreciated by those skilled in the art that various modifications and alternatives to those details could be developed in light of the overall teachings of the disclosure. For example, more than one linear phased array of ultrasonic transducers can be employed simultaneously and any number of scan patterns can be used for each examination. Accordingly, the particular embodiments disclosed are meant to illustrative only and not limiting as to the scope of the invention which is to be given the full breadth of the appended claims and any and all equivalents thereof

What is claimed is:

1. A method for inspecting a cylinder component of high-pressure cylinders of steam turbines, wherein the cylinder component has an axial dimension, comprising the steps of:
   supporting a linear phased array of ultrasonic transducers at an axial location along a surface of the cylinder component;
   moving the linear phased array of ultrasonic transducers axially while monitoring linear phased array of ultrasonic transducers' output to identify an axial location to be monitored;
   fixing the linear phased array of ultrasonic transducers at the axial location to be monitored;
   moving the linear phased array of ultrasonic transducers circumferentially around the surface of the cylinder component at least 360° at the axial location while noting outputs of the linear phased array of ultrasonic transducers indicative of fatigue induced flaws in a wall of the cylinder component;
   routing the linear phased array of ultrasonic transducers circumferentially around the fixed axial location where a most significant flaw was noted from the linear phased array of ultrasonic transducers outputs during the step of moving the linear phased array of ultrasonic transducers circumferentially; and
   successively focusing the linear phased array of ultrasonic transducers at different depths in the wall where the most significant flaw was noted to further characterize the depth and size of the flaw.

2. The method of claim 1, wherein the linear phased array of ultrasonic transducers are supported on an inside surface of the cylinder component.

3. The method of claim 1, wherein the linear phased array of ultrasonic transducers are supported on an outside surface of the cylinder component.

4. The method of claim 1 including the step of remotely positioning the linear phased array of ultrasonic transducers on the surface of the cylinder component.

5. The method of claim 1 including the step of remotely recording a circumferential position of the linear phased array of ultrasonic transducers on the surface of the cylinder component.

6. The method of claim 5 including the step of coordinating the recorded circumferential position to corresponding outputs of the linear phased array of ultrasonic transducers.

7. The method of claim 1, wherein a significant indication of a potential flaw is detected including the step of performing a magnetic rubber nondestructive examination on a surface of a stream inlet nozzle over an area where the significant indication of a potential flaw is detected.

8. The method of claim 1 wherein the cylinder component is a main steam inlet nozzle sleeve on high-pressure outer cylinder of the steam turbines.

9. The method of claim 8 wherein the axial location to be monitored is a trepan region of the main steam inlet nozzle.

10. The method of claim 1 wherein the axial location to be monitored is a nozzle chamber to cylinder welds on a high-pressure inner cylinder of a steam turbine.

11. The method of claim 1 including the steps of:
   radially moving the linear phased array of ultrasonic transducers to a new radial position adjacent a radial location on the surface of the cylindrical component previously scanned;
   fixing the linear phased array of ultrasonic transducers at the new radial position;
   moving the linear phased array of ultrasonic transducers circumferentially around the surface of the cylinder component at least 360° while noting outputs of the linear phased array of ultrasonic transducers indicative of fatigue induced flaws in the wall of the cylinder component at the new radial position;
   routing the linear phased array of ultrasonic transducers circumferentially around the new radial position where a most significant flaw was noted from the linear phased array of ultrasonic transducers' outputs during the immediately preceding step of moving the linear phased array of ultrasonic transducers circumferentially; and
   successively focusing the linear phased array of ultrasonic transducers at different depths in the wall to further characterize the depth and size of the flaw at a circumferential position routed in the immediately preceding step of routing the linear phased array of ultrasonic transducers.

12. The method of claim 1 wherein the cylinder component is a main steam inlet nozzle sleeve on a high-pressure outer cylinder of the steam turbines and the axial location to be monitored is the trepan region on the main steam inlet nozzle sleeve including the steps of
   supporting the linear phased array of ultrasonic transducers on an outside surface of the main steam inlet nozzle sleeve upstream of the trepan region; and
   reflecting signals from the phased array of ultrasonic transducers off of an inside wall of the main steam inlet nozzle sleeve, to the trepan region.

13. The method of claim 12 wherein the supporting and reflecting steps are conducted without disassembling the cylinder component.

14. The method of claim 13 wherein the supporting step of supporting the linear phased array of ultrasonic transducers on an outside surface of the main steam inlet nozzle sleeve and the step of reflecting signals are conducted from outside the high-pressure outer cylinder.

* * * * *